United States Patent
Biedermann et al.

(10) Patent No.: US 10,010,361 B2
(45) Date of Patent: Jul. 3, 2018

(54) BONE ANCHOR

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 1014 days.

(21) Appl. No.: 13/919,966

(22) Filed: Jun. 17, 2013

(65) Prior Publication Data

US 2014/0005731 A1  Jan. 2, 2014

Related U.S. Application Data

(60) Provisional application No. 61/661,243, filed on Jun. 18, 2012.

(30) Foreign Application Priority Data

Jun. 18, 2012 (EP) ..................... 12172417

(51) Int. Cl.
  *A61B 17/86* (2006.01)
  *A61B 17/68* (2006.01)
(52) U.S. Cl.
  CPC ........ *A61B 17/8605* (2013.01); *A61B 17/686* (2013.01); *A61B 17/8685* (2013.01);
  (Continued)

(58) Field of Classification Search
  CPC . A61B 17/702; A61B 17/864; A61B 17/8625; A61B 17/866; A61B 17/8685;
  (Continued)

(56) References Cited

U.S. PATENT DOCUMENTS 5,061,137 A  10/1991 Gourd
5,169,400 A  12/1992 Mühling et al.
(Continued)

FOREIGN PATENT DOCUMENTS

CN  2453859 Y  10/2001
CN  102413777 A  4/2012
(Continued)

OTHER PUBLICATIONS

Extended European Search Report for Application No. EP12172417.3, dated Feb. 6, 2013, 10 pages.
(Continued)

*Primary Examiner* — Anu Ramana
(74) *Attorney, Agent, or Firm* — Lewis Roca Rothgerber Christie LLP (57) ABSTRACT

A bone anchor is provided comprising an anchor member having an open first end, a second end and a tubular section between the first end and the second end, a longitudinal axis extending from the first end to the second end, and a bone engagement structure for engaging the bone in at least a portion of the tubular section, wherein the anchor member is made of a first material. The bone anchor also comprises a core member having a first end and a second end and being insertable into the anchor member and connectable thereto, wherein the core member is made of a second material that is different from the first material.

24 Claims, 7 Drawing Sheets

(52) U.S. Cl.
CPC .......... *A61B 17/864* (2013.01); *A61B 17/866* (2013.01); *A61B 17/8635* (2013.01)

(58) Field of Classification Search
CPC ............ A61B 2017/043; A61B 17/844; A61B 17/3417; A61B 17/3431
See application file for complete search history.

(56) References Cited

U.S. PATENT DOCUMENTS

| | | | |
|---|---|---|---|
| 5,584,695 | A | 12/1996 | Lal Sachdeva et al. |
| 5,876,434 | A | 3/1999 | Flomenblit et al. |
| 6,168,597 | B1 | 1/2001 | Biedermann et al. |
| 7,235,079 | B2 | 6/2007 | Jensen et al. |
| 7,879,036 | B2 | 2/2011 | Biedermann et al. |
| 8,292,932 | B2 | 10/2012 | Matthis et al. |
| 8,974,508 | B2 * | 3/2015 | Stephan ............... A61B 17/686 606/304 |
| 2006/0264954 | A1 | 11/2006 | Sweeney, II et al. |
| 2007/0293866 | A1 | 12/2007 | Stoeckel et al. |
| 2008/0294204 | A1 | 11/2008 | Chirico et al. |
| 2009/0131992 | A1 | 5/2009 | Greenhalgh et al. |
| 2009/0171396 | A1 | 7/2009 | Baynham et al. |
| 2010/0076498 | A1 | 3/2010 | Tyber et al. |
| 2010/0082071 | A1 | 4/2010 | Moumene |
| 2010/0228301 | A1 | 9/2010 | Greenhalgh et al. |
| 2010/0261034 | A1 | 10/2010 | Cardarelli |
| 2011/0319946 | A1 * | 12/2011 | Levy ................. A61B 17/7035 606/309 |
| 2012/0010668 | A1 * | 1/2012 | Shimko ............. A61B 17/7032 606/305 |
| 2012/0078369 | A1 | 3/2012 | Hart |
| 2012/0184993 | A1 | 7/2012 | Arambula et al. |
| 2012/0245704 | A1 | 9/2012 | Childs |
| 2012/0295129 | A1 | 11/2012 | Kato et al. |
| 2013/0245697 | A1 | 9/2013 | Hulliger |
| 2014/0172026 | A1 | 6/2014 | Biedermann et al. |
| 2014/0172027 | A1 | 6/2014 | Biedermann et al. |

FOREIGN PATENT DOCUMENTS

| | | |
|---|---|---|
| EP | 0611557 A2 | 8/1994 |
| EP | 1 743 587 A1 | 1/2007 |
| EP | 2 446 842 A1 | 5/2012 |
| JP | 2005-516721 A | 6/2005 |
| JP | 2014-110486 A | 6/2014 |
| KR | 10-2010-0108339 A | 10/2010 |
| WO | WO 95/15726 | 6/1995 |
| WO | WO 03/068063 A1 | 8/2003 |
| WO | WO 2007/101267 A1 | 9/2007 |
| WO | WO 2007/110863 A2 | 10/2007 |
| WO | WO 2008/004057 A2 | 1/2008 |
| WO | WO 2008/024373 A2 | 2/2008 |
| WO | WO 2009/059227 A1 | 5/2009 |
| WO | WO 2009/079329 A2 | 6/2009 |
| WO | WO 2009/120969 A2 | 10/2009 |
| WO | WO 2010/105174 A1 | 9/2010 |
| WO | WO 2011/056990 A2 | 5/2011 |
| WO | WO 2011/092909 A1 | 8/2011 |

OTHER PUBLICATIONS

Korean Office action for Application No. 2013-0067979, dated Apr. 21, 2016 (7 pages) and English translation (5 pages).
European Search Report and Opinion issued by the EPO for EP 12172417.3 dated Nov. 14, 2012 (6 pages).
Non-Final Office action for U.S. Appl. No. 14/098,425, dated Jan. 3, 2017, 10 pages.
Final Office action for U.S. Appl. No. 14/098,425, dated Jul. 13, 2017, 13 pages.
Non-Final Office action for U.S. Appl. No, 14/098,425, dated Nov. 30, 2017, 16 pages.

* cited by examiner

BONE ANCHOR

CROSS-REFERENCE TO RELATED APPLICATIONS

The present disclosure claims the benefit of U.S. Provisional Patent Application Ser. No. 61/661,243, filed Jun. 18, 2012, the contents of which are hereby incorporated by reference in their entirety, and claims priority from European Patent Application EP 12172 417.3, filed Jun. 18, 2012, the contents of which are hereby incorporated by reference in their entirety.

BACKGROUND

Field

The invention relates to a bone anchor comprising an anchor member with a tubular section and a bone engagement structure for engaging the bone in at least a portion of the tubular section and further comprising a core member being insertable into the anchor member and connectable thereto. The anchor member is made of a material that is more flexible than a material of the core member. In particular, the bone anchor can be used in a bone fixation or stabilization arrangement and it is especially suitable for anchoring fixation or stabilization devices in osteoporotic bones.

Description of Related Art

US 2010/082071 A1 describes a composite screw preferably made of a metallic pin embedded in a polymeric tubular structure having outwardly facing threads, wherein the metallic pin comprises a screw head, an intermediate shaft and a screw tip, and the polymeric threaded tube is either molded onto the metallic shaft or the thread is machined after molding a polymeric structure onto the shaft. In preferred embodiments, the composite screw has a variable stiffness along the screw shaft from the tip to the head. Hence, the composite screw is meant to reduce the stiffness of the screw by introducing a polymeric thread.

U.S. Pat. No. 6,168,597 B1 describes a bone screw with a threaded shaft portion, a longitudinal bore provided in the shaft, a head and a flared portion which flares towards the free end opposite to the head. Slits extending parallel to the longitudinal axis are provided in this portion of the threaded shaft. An expanding member comprises a top portion forming the top of the bone screw and the shaft. The expanding member is first pushed into the bore and then the screw together with the expanding member is screwed into the bone. Thereafter, the bone screw can be expanded within the bone by pulling the top portion of the expanding member into the longitudinal bore of the shaft portion.

SUMMARY

It is the object of the invention to provide an improved bone anchor that is particularly useful for the application in weak osteoporotic bones.

The anchor member of the bone anchor is made of a material that is more flexible than the material of the core member. Therefore, an overall stiffness of the bone anchor is reduced compared to the stiffness of a bone anchor that consists of metallic components only. Preferably, the material of the anchor member is a polymer material and the material of the core member is a metallic material.

The bone anchor has the advantage that the anchor member can be inserted separately into the bone and thereafter the core member can be inserted. Because the core member can be inserted by a sliding motion into the anchor member without any screwing operation, the insertion of the core member can be carried out quickly and in a simple manner. Alternatively, the anchor member and the core member can be pre-assembled and screwed into the bone as a whole.

By selecting an appropriate combination of materials in regard of the anchor member and the core member, an appropriate stiffness of the bone anchor can be achieved.

The bone anchor can be used with all known polyaxial receiving parts and other stabilization devices. Because the head is made from a material that is commonly used for stabilization and/or fixation devices, the head can be effectively connected and fixed to such stabilization and/or fixation devices.

The anchor member provides for an improved long-term anchoring in the bone.

BRIEF DESCRIPTION OF THE DRAWINGS

Further features and advantages will become apparent from the description of embodiment by means of the accompanying drawings. In the drawings:

FIG. 10a shows a cross-sectional view of mounting the core member to the anchor member inserted into the bone according to the first embodiment.

FIG. 10b shows an enlarged portion of FIG. 10a.

FIG. 11a shows a cross-sectional view of further inserting the core member to the anchor member while the anchor member is expanded according to the first embodiment.

FIG. 11b shows an enlarged portion of FIG. 11a.

FIG. 12a shows a still further step of inserting the core member while further expanding the anchor member according to the first embodiment.

FIG. 12b shows an enlarged portion of FIG. 12a.

FIG. 13a shows a cross-sectional view of the last step of connecting the core member to the anchor member wherein the core member is fully inserted into the anchor member according to the first embodiment.

FIG. 13b shows an enlarged portion of FIG. 13a.

DETAILED DESCRIPTION

Figure 1:
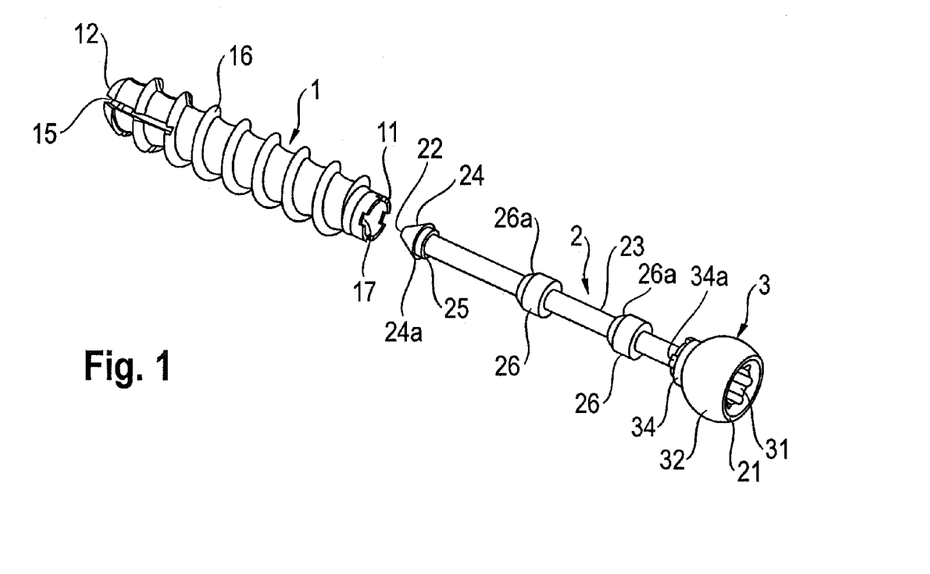
FIG. 1 shows a perspective exploded view of the bone anchor according to a first embodiment.
Figure 2:
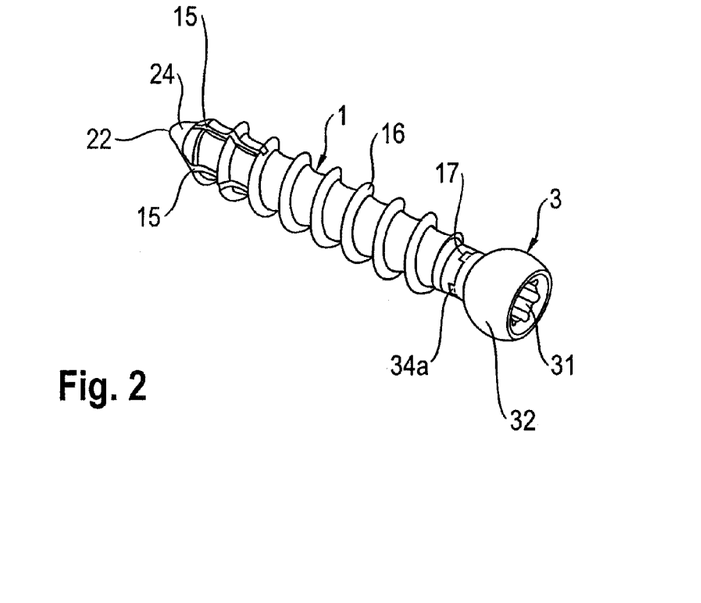
FIG. 2 shows a perspective view of the bone anchor according to FIG. 1 in an assembled state.

As shown in FIGS. 1 and 2, the bone anchor according to a first embodiment comprises an anchor member 1, in the form of a screw member and a core member 2. The core member 2 can be inserted into the anchor member 1 and connected thereto to form the bone anchor.

Figure 3:
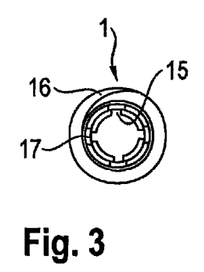
FIG. 3 shows a top view of the first end of the anchor member according to the first embodiment.
Figure 4:
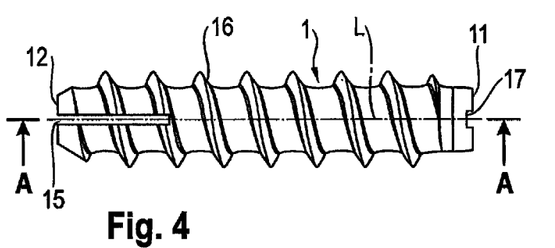
FIG. 4 shows a side view of the anchor member according to the first embodiment.
Figure 5:
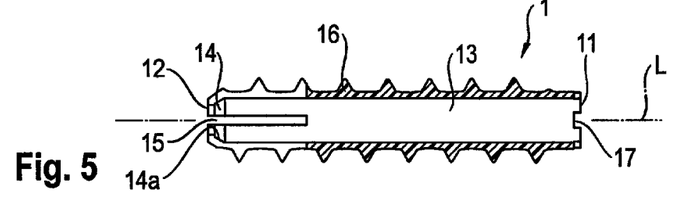
FIG. 5 shows a cross-sectional view of the anchor member according to line A-A in FIG. 4.

As further shown in FIGS. 3 to 5, the anchor member 1 has a first end 11, an opposite second end 12 and a longitudinal axis L extending through the first end 11 and the second end 12. The anchor member 1 is formed as a tubular member and has a first section 13 with a first inner diameter, the first section 13 extending from the first end 11 to a distance from the second end 12. In a second section 14 adjacent the second end 12, the inner diameter is gradually reduced towards the second end 12. The second section 14 comprises a tapered inner surface 14a tapering towards the second end 12. At the second end 12, at least two, preferably three or four slits 15 are provided that are open to the second end 12 and extend into the first section 13. The slits 15 are substantially parallel to the longitudinal axis L. By means of the slits 15, the anchor member 1 is rendered flexible in the region of its second end 12 as described below.

Figures 13A, 13B:
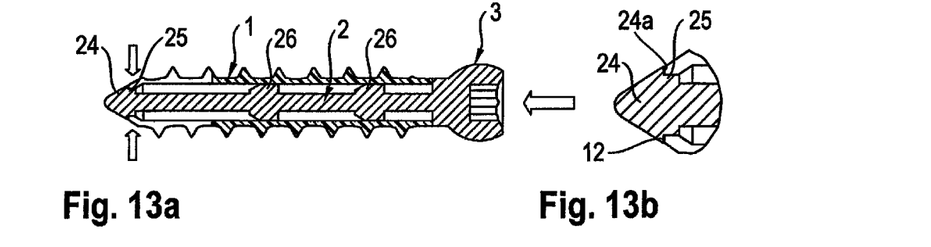

The front face of the second end 12 defines an abutment for a portion of the core member 2 when the core member 2 is fully inserted as shown in FIGS. 1 and 13a, 13b.

At least a portion of the outer surface on the anchor member 1 is provided with a bone thread 16. Instead of the bone thread 16, another bone engagement structure may be provided, such as, for example, barbs or a textured surface.

At the first end 11, a plurality of recesses 17 are extending from the front face of the first end 11 into the first tubular section 13 and form engagement portions for a form-fit engagement with the head 3 of the core member 2, described below.

The anchor member 1 is made of a material that has a smaller modulus of elasticity compared to a modulus of elasticity of the material of the core member 2. Preferably, the anchor member 1 is made of a polymer material, in particular a biocompatible polymer material. For example, the material may be selected from the group of polyaryletherketones PAEK including polyetheretherketone PEEK, polyetherketoneketone PEKK and polyetherketone PEK. However, other polymeric materials may also be used. The extent to which the anchor member 1 is expandable at its second end 12 can be adjusted during manufacturing by selecting an appropriate material, the wall thickness of the anchor member 1, and the length and the width of the slits 15.

Figure 6:
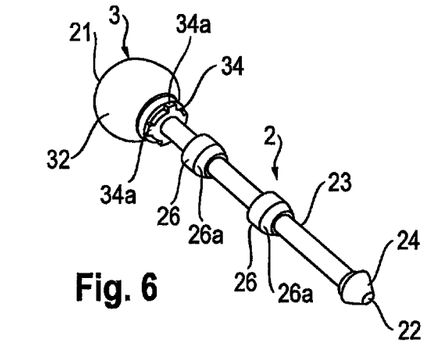
FIG. 6 shows a perspective view of the core member of the bone anchor according to the first embodiment.
Figure 7:
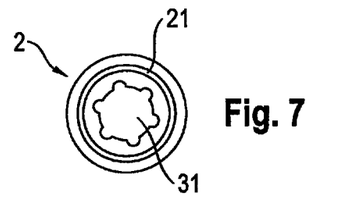
FIG. 7 shows a top view of the first end of the core member of the bone anchor according to the first embodiment.
Figure 8:
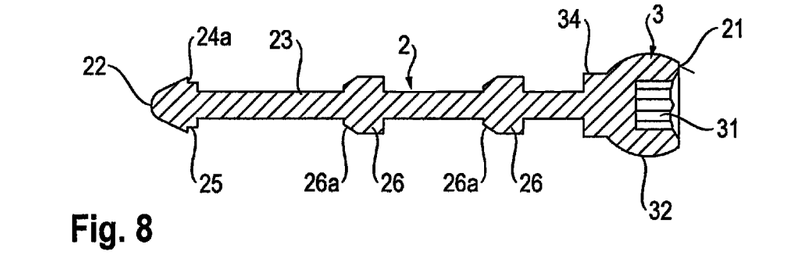
FIG. 8 shows a cross-sectional view of the core member of FIG. 6 wherein the section has been taken in a plane containing the longitudinal axis.
Figure 9:
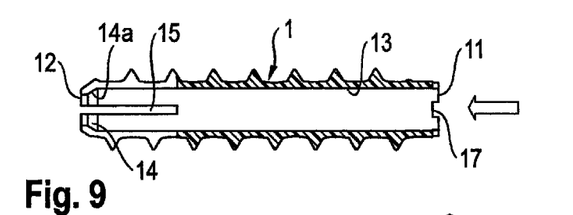
FIG. 9 shows a cross-sectional view of the anchor member of the bone anchor according to the first embodiment in a first step of anchoring the bone anchor in the bone.

As further shown in FIGS. 6 to 8, the core member 2 comprises a first end 21, an opposite second end 22 and a substantially rod-shaped central portion 23. Adjacent to the first end 21, the head 3 of the anchor is provided. The head 3 has an engagement portion 31 at the free end that forms the first end 21, with a recess that can be engaged with a tool, such as a torx-shaped recess or a hexagon-shaped recess. The head 3 further comprises a spherically-shaped surface portion 32. The diameter of the spherically-shaped surface portion 32 decreases towards the rod-shaped central portion 23. The head 3 serves for connecting the bone anchor with other devices, such as stabilization or fixation devices, for example with a receiving part of a polyaxial bone anchor or with a plate member. Between the spherically-shaped outer surface portion 32 and the rod-shaped central portion 23, a neck portion 34 is provided that has a smaller diameter than the spherically-shaped outer surface portion and a larger diameter than the rod-shaped central portion 23. The neck portion 34 has an outer diameter so that it fits into the tubular anchor member 1 at the first end 11. As shown in FIG. 6, projections 34a projecting in a radial and axial direction are present in positions corresponding to the recesses 17 at the first end 11 of the anchor member 1. The projections 34a are configured to engage the recesses 17 and achieve a form-fit connection between the core member 2 and the anchor member 1 at the first end 11 of the anchor member 1. By means of the engagement of the projections 34a and the recesses 17, the core member 2 can be fixed to the anchor member 1 so that the core member 2 cannot rotate with respect to the anchor member 1.

At the second end 22, the core member 2 comprises a tip 24. The tip 24 tapers with a cone angle towards the second end 22 wherein the cone angle corresponds substantially to the cone angle of the tapered portion 14a of the anchor member 1. Between the rod-shaped central portion 23 and the tip 24, a cylindrical portion 25 is present that has a smaller diameter than a base of the tip 24 such that, as can be seen in FIGS. 2 and 13a-13b, the base 24a of the tip 24 abuts against the front face of the second end 12 of the anchor member 1.

One or more guide portions 26 may be provided on the rod-shaped central portion 23, wherein the guide portions 26 have a substantially cylindrical shape with a slanted surface 26a that tapers towards the second end 22. The outer diameters of the guide portions 26 are only slightly smaller than the inner diameter of the first section 13 of the anchor member 1. Therefore, the guide portions 26 provide guidance by sliding along the inner wall of the anchor member 1 when the core member 2 is inserted into the tubular anchor member 1. The tapered surfaces 26a facilitate the insertion of the core member 2 into the anchor member 1. The guide portions 26 may be monolithically formed with the core member 2 or may be separate parts that are fixed to the core member 2. They may also be omitted.

The core member 2 is made of a material that is preferably stiffer than the material of the anchor member 1, i.e. has a higher modulus of elasticity. For example, the core member 2 is made of a metallic material such as titanium, stainless steel, a body compatible metal alloy, such as, for example, a Mi-Ti alloy, such as Nitinol.

Figure 14:
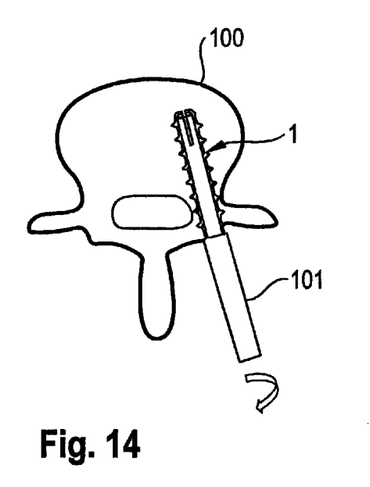
FIGS. 14 to 16 show steps of anchoring the bone anchor according to the first embodiment in a pedicle of a vertebra.

A first embodiment of a method of using the anchor member 1 will be explained with reference to FIGS. 9 to 16. First, as shown in FIG. 14, the anchor member 1 is inserted into a bone, a bone part or a vertebra 100. A core hole may be prepared in advance. A tool 101 may be used that engages the anchor member 1. The engagement portion 17 that serves for a form-fit connection to the anchor member 1 may also be used as an engagement portion for a tool. Other engagement portions (not shown) may be provided.

Figures 10A, 10B:
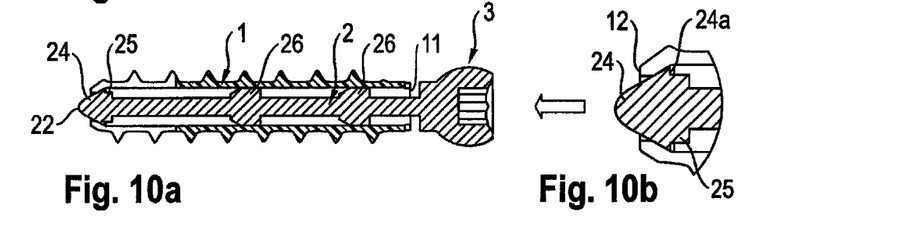

In a second step, as shown in FIGS. 10a and 10b, the core member 2 is inserted with the tip 24 facing the anchor member 1 into the anchor member 1 until the tip 24 abuts against the tapered portion 14a on the inner wall of the anchor member 1 at the second end 12. During insertion, the core member 2 slides along the inner surface of the anchor member 1 while it is guided by the inner wall of the first section 13 contacting the guide portions 26.

Figures 11A, 11B:
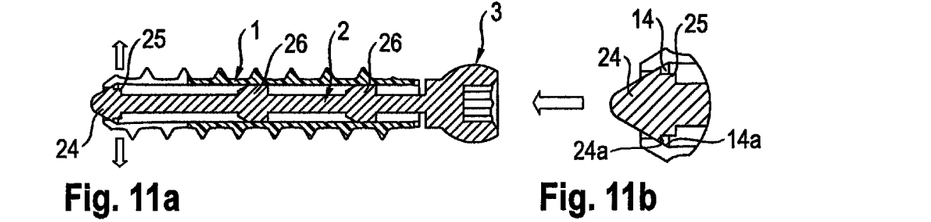

Next, as shown in FIGS. 11a and 11b, further advancement of the core member 2 into the anchor member 1 results in an expansion of the anchor member 1 at the second end 2 because the outer diameter of the base 24a of the tip 24 is greater than the inner diameter of the tubular anchor member 1 at the second end 12.

Figures 12A, 12B:
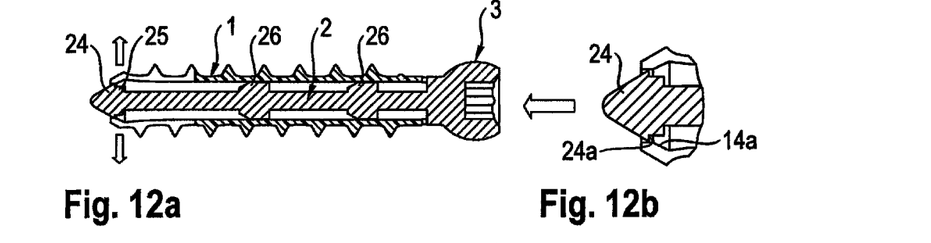

In a further step, as shown in FIGS. 12a and 12b, the further advancement of the core member 2 into the anchor member 1 allows the tip 24 to exit from the anchor member 1, thereby further expanding the anchor member 1 at the second end 12.

Finally, as shown in FIGS. 13a and 13b, when the core member 2 is still further advanced, the expanded portion of the anchor member 1 snaps back so that the anchor member 1 abuts with its front face at the second end 12 against the base surface 24a of the tip 24 with the cylindrical portion 25 extending through the second end 12 and forming an abutment for the anchor member 1 in a radial direction. The base surface 24a of the tip 24 forms an abutment in the longitudinal direction for the second end 12 of the anchor member 1. The dimensions of the rod-shaped central portion 23 is such that in the fully inserted configuration as shown in FIG. 13a, the projections 34a of the neck portion 34 fully engage the recesses 17 so that the core 2 is rotationally fixed with respect to the anchor member 1.

Figure 15:
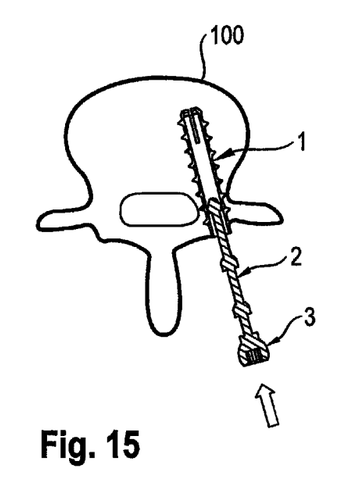
Figure 16:
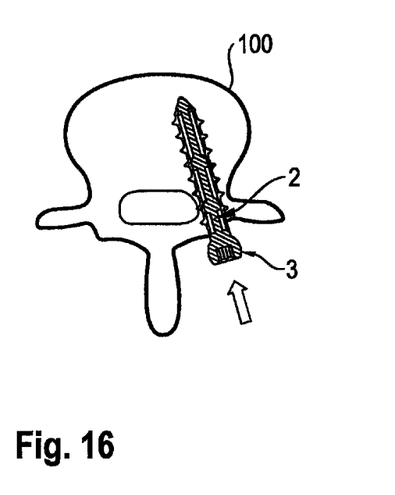

FIGS. 14 to 16 show a method of use as described before with the application of the bone anchor to the pedicle of a vertebra 100. FIG. 14 shows the anchor member 1 being first inserted with a tool 101 into a pedicle. Then, the tool is removed and the core member 2 is inserted as shown in FIG. 15. FIG. 16 shows the final configuration where the core member 2 has been fully inserted into the anchor member 1.

In a second embodiment of a method of use the pre-assembled anchor member 1 with the core member 2 as depicted in FIG. 13a are inserted as a whole assembly into the bone.

Figure 17:
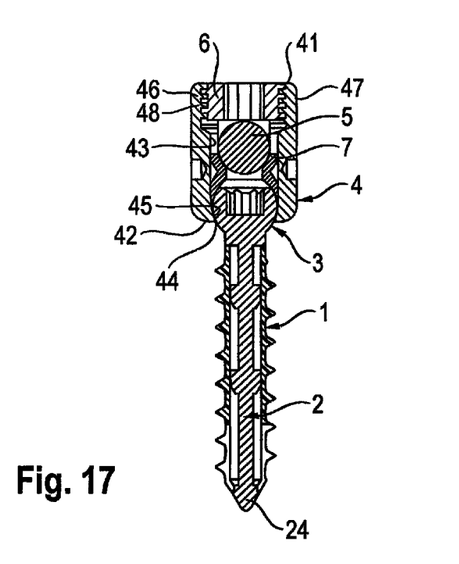
FIG. 17 shows a cross-section view of a polyaxial bone anchoring device with a bone anchor according to the first embodiment.

A first application of the bone anchor together with a stabilization device is shown in FIG. 17. The bone anchor according to the first embodiment is received in a receiving part 4 of a polyaxial bone anchor. The receiving part 4 is substantially cylindrical and comprises a top end 41, a bottom end 42 and a coaxial bore 43 extending from the top end 41 to a distance from the bottom end 42. The bore 43 narrows towards the bottom end 42 and provides an opening 44. Near the bottom end, a seat 45 is provided for pivotably receiving the head 3. A U-shaped recess extends from the top end 41 to a distance from the top end 41 for receiving a rod 5. By means of the U-shaped recess two free legs 46, 47 are provided which have an internal thread 48 for cooperating with a locking member 6. Further, a pressure member 7 is provided that exerts pressure onto the head 3 such that the head 3 can be locked in a certain angular position by tightening the locking member 6. The bone anchor may be used with other types of receiving parts and other designs for polyaxial bone screws. Also the head 3 of the core member 2 may be designed such that it comprises a section for receiving a rod and for receiving a locking member to fix the rod as known from monoaxial bone screws.

Figure 18:
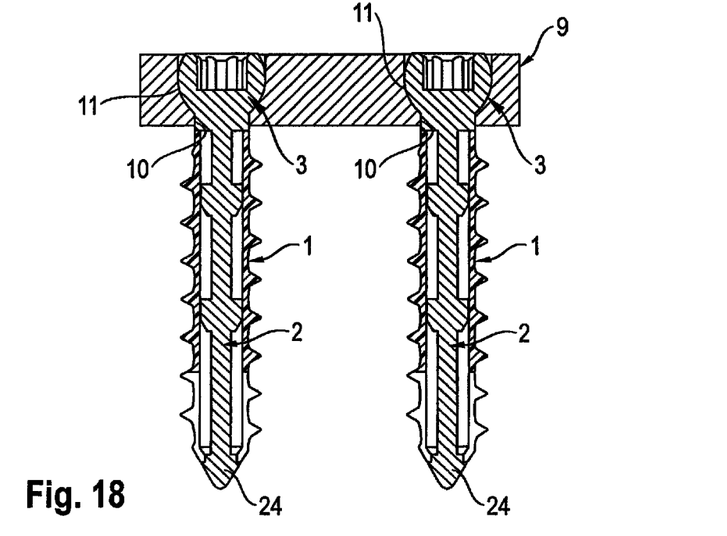
FIG. 18 shows a cross-sectional view of a bone plate with the bone anchor according to the first embodiment.

A second example of application is shown in FIG. 18 wherein the bone anchors according to the first embodiment are used together with a bone plate 9 that has holes 10 and seat portions 11 for receiving the head 3 of each bone anchor 2. Various configurations of such bone plates are conceivable. Also in this case, the head 3 may be adapted in its shape to correspond to receiving portions provided in the bone plate.

Figures 19, 20:
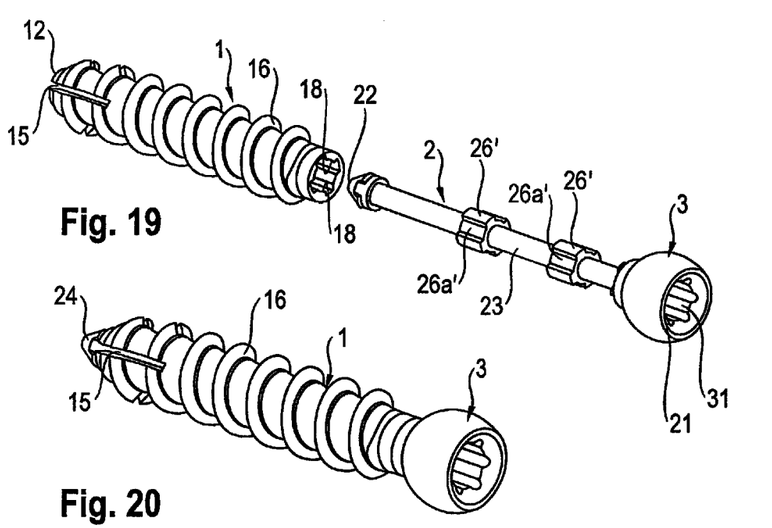
FIG. 19 shows a perspective exploded view of the bone anchor according to a second embodiment.
FIG. 20 shows a perspective view of the bone anchor according to the second embodiment in an assembled state.
Figure 21:
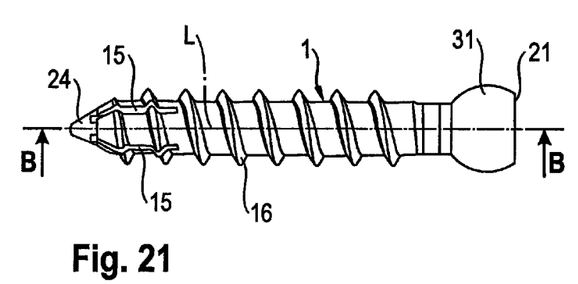
FIG. 21 shows a side view of the bone anchor according to the second embodiment.
Figure 22:
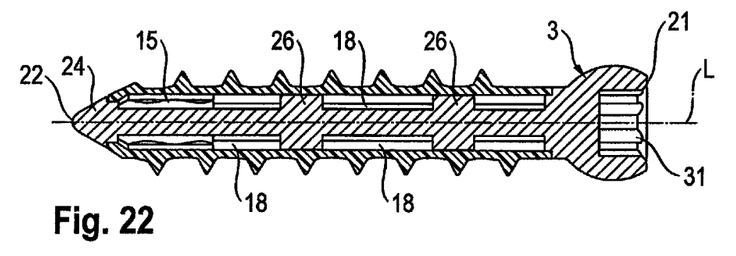
FIG. 22 shows a cross-sectional view of the bone anchor according to the second embodiment along line B-B in FIG. 21.
Figure 23:
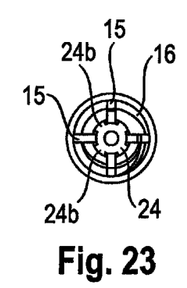
FIG. 23 shows a bottom view of the second end of the bone anchor according to the second embodiment.

Referring to FIGS. 19 to 21, a second embodiment of the bone anchor is shown. The anchor member 1' and the core member 2' each comprise structures that cooperate which each other to enhance the fixation of the core member 2' to prevent a rotational and axial movement of the parts.

The anchor member 1' will be described more in detail with reference to FIGS. 24 to 29. Parts and portions that are identical to the parts and portions of the previous embodiment are indicated with the same reference numerals and the description thereof will not be repeated. The anchor member 1' comprises an internal guiding structure provided by longitudinally extending rib-like projections 18. The rib-like projections 18 extend from the first end 11 to a distance from the second end 12. Preferably, the rib-like projections 18 extend only up to the end of the slits 15 closest to the first end 11 so that the flexible portion of the anchor member 1' does not have rib-like projections 18.

Figure 24:
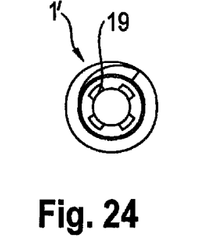
FIG. 24 shows a top view of the first end of the anchor member of the bone anchor according to the second embodiment.
Figure 25:
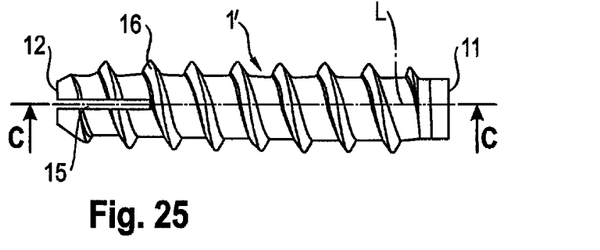
FIG. 25 shows a side view of the anchor member according to the second embodiment.
Figures 26, 27:
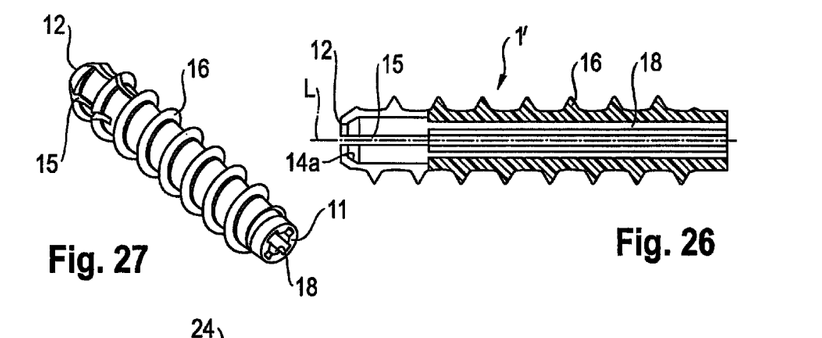
FIG. 26 shows a cross-sectional view of the anchor member according to the second embodiment along line C-C in FIG. 25.
FIG. 27 shows a perspective view from the first end of the anchor member according to the second embodiment.
Figure 28:
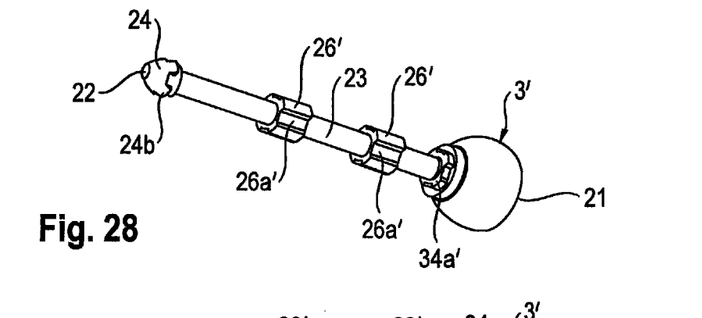
FIG. 28 shows a perspective view of the core member of the bone anchor according to the second embodiment.
Figure 29:
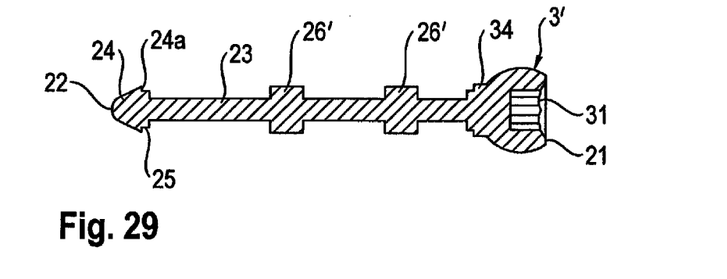
FIG. 29 shows a cross-section view of the core member according to the second embodiment, the section being taken in a plane containing the longitudinal axis.

For example, four rib-like projections 18 are arranged at a substantially 90° with respect to each other so that they form a cross arrangement. In addition, at the second end 12, a plurality of recesses 19, for example four recesses 19, are arranged in the end face of the end 12, as shown in FIG. 24. The recesses 19 serve for engagement with corresponding portions on the core member 2'. The head 3 has at its side facing the rod-shaped portion 23 projections 34a' that are arranged and configured to engage the tubular section 13 that has the rib-like projections 18.

The core member 2' has on its rod-shaped central portion 23 at least one, preferably a plurality of spaced apart guiding portions 26'. The maximum outer diameter of the guiding portion 26' is slightly smaller than the inner diameter of the anchor member 2' in the space between the rib-like projections 18. The guiding members 26' comprise longitudinal grooves 26a' that are arranged spaced apart form each other in a circumferential direction and at positions corresponding to the positions of the projections 18. Hence, the grooves 26a' are configured to engage the rib-like projections 18.

At the base of the tip 24 facing towards the first end 22, there are projections 24b projecting outward and in the direction towards the first end 21 of the core member 2'. The projections 24b are configured to engage in the recesses 19 of the anchor member.

By means of the above described form-fit connection between the core member 2' and the anchor member 1' a structure is provided that prevents rotation of the core member 2' relative to the anchor member 1' and also prevents axial displacement of the members.

Other designs of such engagement structures are possible. For example, more or less than four projections and grooves can be provided. The inner wall of the anchor member 1' can have an elliptic or another contour that prevents rotation when engaging a corresponding contour of the core member 2'.

Further modifications of the embodiments are possible. For example, the core member can be made of two or more parts. The head can be made as a separate part that can be connected to the core member. Also, the head 3 may be a part of the anchor member.

The second end of the anchor member may be closed and a tip at the core member may be omitted. In this case, the structure is provided that fixes the core member to the anchor member.

The head may have a different shape dependent of the intended use of the bone anchor. The materials and the combination of materials of the second embodiment may be the same as in the first embodiment.

The invention claimed is:

1. A bone anchor comprising:
an anchor member having a first end and a second end, a tubular section extending along a longitudinal axis between the first end and the second end and having at least one slit open to the second end and extending towards the first end, the slit defining an expandable portion, and a bone engagement structure on the tubular section for engaging a bone, wherein the anchor member comprises a first material, and wherein an entire length of the anchor member is measured from the first end to the second end; and
a core member having a length defined between first and second ends of the core member, the length of the core member being greater than the entire length of the anchor member along the longitudinal axis, the core member having a tip defining the first end of the core member, a head defining the second end of the core member, and a central portion extending along an axis between the first end and the second end of the core member, the core member being insertable into the anchor member and connectable thereto, wherein when the core member and the anchor member are connected, at least a portion of the tip of the core member is configured to protrude out of the second end of the anchor member while at least a portion of the head of the core member remains positioned outside of the first end of the anchor member;
wherein the core member comprises a second material that is different from the first material, and wherein the tip and the head each has a width in a direction perpendicular to the axis of the core member that is greater than a width of the central portion of the core member in the direction perpendicular to the axis of the core member;
wherein the expandable portion of the anchor member has a first position and a second position expanded from the first position, and wherein the tip is movable through a region of the expandable portion while the expandable portion remains in the first position, and is movable through the second end of the anchor member by expanding an opening at the second end; and
wherein the tip of the core member is configured to be inserted into the first end of the anchor member and moved through the expandable portion of the anchor member to the second end of the anchor member.

2. The bone anchor of claim 1, wherein the first material exhibits greater flexibility than the second material.

3. The bone anchor of claim 1, wherein the first material comprises a polymeric material.

4. The bone anchor of claim 1, wherein the second material comprises a metallic material.

5. The bone anchor of claim 1, wherein the bone engagement structure comprises a bone thread.

6. The bone anchor of claim 1, wherein the first end and the second end of the anchor member form open ends of the tubular section and wherein the expandable portion of the anchor member is expandable in a direction away from the longitudinal axis.

7. The bone anchor of claim 1, wherein the anchor member has at least two slits.

8. The bone anchor of claim 1, wherein an inner wall of the anchor member comprises a tapered section adjacent the second end of the anchor member, the tapered section resulting in a reduced width of the inner wall of the anchor member towards the second end, the width measured in a direction perpendicular to the longitudinal axis.

9. The bone anchor of claim 1, wherein the anchor member comprises a head engagement structure at the first end of the anchor member configured to engage the head of the core member.

10. The bone anchor of claim 9, wherein the head engagement structure includes at least one recess extending from the first end of the anchor member into the tubular section.

11. The bone anchor of claim 1, wherein the head of the core member has a spherically-shaped outer surface portion.

12. The bone anchor of claim 11, wherein the head of the core member comprises an engagement portion for engaging the anchor member.

13. The bone anchor of claim 1, wherein the tip of the core member tapers towards the second end of the core member.

14. The bone anchor of claim 1, wherein a maximum outer diameter of the tip of the core member is greater than an inner diameter of the tubular section at the second end of the anchor member.

15. The bone anchor of claim 1, wherein the core member comprises an abutment portion that cooperates with an abutment portion of the anchor member to prevent movement of the tip of the core member towards the first end of the anchor member when the core member is inserted into and connected to the anchor member.

16. The bone anchor of claim 1, wherein an inner wall of the tubular section of the anchor member has a contour that cooperates with a corresponding contour of the core member in such a manner that rotation of the core member relative to the anchor member is prevented when the core member is inserted into the anchor member and when the core member is translationally moveable relative to the anchor member.

17. The bone anchor of claim 16, wherein the inner wall of the tubular section comprises at least one longitudinally extending projection and the core member has at least one corresponding longitudinal groove configured to prevent rotation of the core member relative to the anchor member when the core member is inserted into the anchor member and when the core member is translationally moveable relative to the anchor member.

18. The bone anchor of claim 1, wherein the tip of the core member is configured to contact an inner wall of the expandable portion of the anchor member to expand the opening at the second end of the anchor member.

19. A method for connecting a bone anchor to a bone, the bone anchor comprising an anchor member having a first end and a second end, a tubular section extending along a longitudinal axis between the first end and the second end and having at least one slit open to the second end and extending towards the first end, the slit defining an expandable portion, and a bone engagement structure on the tubular section for engaging a bone, wherein the anchor member comprises a first material, and wherein an entire length of the anchor member is measured from the first end to the second end, and a core member having a length defined between first and second ends of the core member, the length of the core member being greater than the entire length of the anchor member along the longitudinal axis, the core member having a tip defining the first end of the core member, a head defining the second end of the core member, and a central portion extending along an axis between the first end and the second end of the core member, wherein the core member comprises a second material that is different from the first material, and wherein the tip and the head each has a width in a direction perpendicular to the axis of the core member that is greater than a width of the central portion of the core member in the direction perpendicular to the axis of the core member, the method comprising:
  inserting the anchor member into a bone;
  connecting the core member to the anchor member by inserting the core member into the tubular section of the anchor member, wherein the expandable portion of the anchor member has a first position and a second position expanded from the first position, such that the tip is moved through a region of the expandable portion while the expandable portion remains in the first position, and is then moved through the second end of the anchor member by expanding an opening at the second end, and wherein when the tip is moved through the second end of the anchor member, the expandable portion of the anchor member is configured to snap back from the second position to the first position and abut against a surface of the tip, while at least a portion of the head of the core member remains positioned outside of the first end of the anchor member.

20. The method of claim 19, further comprising inserting the tip of the core member into the first end of the anchor member after the step of inserting the anchor member into the bone.

21. A bone anchor comprising:
  an anchor member having a first end and a second end, a tubular section extending along a longitudinal axis between the first end and the second end and having at least one slit open to the second end and extending towards the first end, the slit defining an expandable portion, and a bone engagement structure on the tubular section for engaging a bone, wherein the anchor member comprises a first material, and wherein an entire length of the anchor member is measured from the first end to the second end; and
  a core member having a length defined between first and second ends of the core member, the length of the core member being greater than the entire length of the anchor member along the longitudinal axis, the core member having a tip defining the first end of the core member, a head defining the second end of the core member, and a central portion extending along an axis between the first end and the second end of the core member, the core member being insertable into the anchor member and connectable thereto,
  wherein the core member comprises a second material that is different from the first material, and wherein the tip and the head each has a width in a direction perpendicular to the axis of the core member that is greater than a width of the central portion of the core member in the direction perpendicular to the axis of the core member;
  wherein the expandable portion of the anchor member has a first position and a second position expanded from the first position, and wherein the tip is movable through a region of the expandable portion while the expandable portion remains in the first position, and is movable through the second end of the anchor member by expanding an opening at the second end; and
  wherein when the tip is moved through the second end of the anchor member, the expandable portion of the anchor member is configured to snap back from the second position to the first position and abut against a surface of the tip, while at least a portion of the head of the core member remains positioned outside of the first end of the anchor member.

22. A bone anchor comprising:
  an anchor member having a first end and a second end, a tubular section extending along a longitudinal axis between the first end and the second end and having at least one slit open to the second end and extending towards the first end, the slit defining an expandable portion, and a bone engagement structure on the tubular section for engaging a bone, wherein the anchor member comprises a first material; and
  a core member having a tip defining a first end of the core member, a head defining a second end of the core member, and a central portion extending along an axis between the first end and the second end of the core member, the core member being insertable into the anchor member and connectable thereto,
  wherein the core member comprises a second material that is different from the first material, and wherein the tip and the head each has a width in a direction perpendicular to the axis of the core member that is greater than a width of the central portion of the core member in the direction perpendicular to the axis of the core member,
  wherein the tip is movable through a region of the expandable portion while the expandable portion remains unexpanded, and is movable through the second end of the anchor member by expanding an opening defined at the second end,
  wherein an inner wall of the tubular section of the anchor member comprises a contour configured to contact a corresponding contour of the core member to restrict rotational movement of the core member relative to the anchor member,
  wherein when the core member is in a first axial position relative to the anchor member where the tip is positioned between the first and second ends of the anchor member, rotational movement of the core member relative to the anchor member is restricted while translational movement of the core member relative to the anchor member along the longitudinal axis is permitted, and
  wherein when the core member is in a second axial position relative to the anchor member where the tip has passed through the second end of the anchor member, both rotational and translational movement of the core member relative to the anchor member are prevented, while at least a portion of the head of the core member remains positioned outside of the first end of the anchor member.

23. The bone anchor of claim 22, wherein the contour of the inner wall of the tubular section comprises at least one projection and/or groove configured to contact at least one groove and/or projection of the contour of the core member to restrict rotational movement of the core member relative to the anchor member while permitting translational movement of the core member relative to the anchor member along the longitudinal axis.

24. The bone anchor of claim 23, wherein the at least one groove and/or projection of the contour of the core member is configured to be inserted inside the inner wall of the tubular section such that the inner wall is positionable between an outer wall of the tubular section and the at least one groove and/or projection of the core member in a radial direction.

* * * * *

UNITED STATES PATENT AND TRADEMARK OFFICE
CERTIFICATE OF CORRECTION

PATENT NO. : 10,010,361 B2
APPLICATION NO. : 13/919966
DATED : July 3, 2018
INVENTOR(S) : Lutz Biedermann et al.

It is certified that error appears in the above-identified patent and that said Letters Patent is hereby corrected as shown below:

On the Title Page
Pg. 2, in Column 2, (56), FOREIGN PATENT DOCUMENTS, Line 5   delete "2014-110486",
insert -- 2014-113486 --

Signed and Sealed this
Thirtieth Day of July, 2019

Andrei Iancu
*Director of the United States Patent and Trademark Office*